United States Patent [19]

McShane et al.

[11] Patent Number: 5,381,801

[45] Date of Patent: Jan. 17, 1995

[54] ELECTROMECHANICAL TACTILE STIMULATION DEVICE WORN ON A BELT FOR THE PREVENTION OF SNORING

[76] Inventors: Jerry M. McShane, 2313 Killarney, Deer Park, Tex. 77536; David W. Spinks, 6842 Cedar Lawn Cir., Pasadena, Tex. 77505

[21] Appl. No.: 107,305

[22] Filed: Aug. 17, 1993

[51] Int. Cl.⁶ .......................... A61F 5/56; A61F 5/37; A41F 9/00; G08B 23/00
[52] U.S. Cl. ................................. 128/848; 128/871; 340/573; 2/315
[58] Field of Search ............... 128/848, 871, 876, 846, 128/870, 869; 2/DIG. 11, 311, 312, 315; 224/253, 251, 240; 600/26, 27; 601/70, 71, 79; 340/573

[56] References Cited

U.S. PATENT DOCUMENTS

| 648,028 | 4/1900 | Hooper . | |
|---|---|---|---|
| 663,825 | 12/1900 | Wilson | 128/871 |
| 746,869 | 12/1903 | Moulton . | |
| 876,491 | 1/1908 | Rohwer | 128/848 |
| 1,354,652 | 10/1920 | Jeffries . | |
| 2,178,128 | 10/1939 | Waite . | |
| 2,627,268 | 2/1953 | Leppich . | |
| 4,616,639 | 10/1986 | Huber | 5/630 |
| 4,788,533 | 11/1988 | Mequignon . | |
| 4,817,636 | 4/1989 | Woods . | |
| 4,848,360 | 7/1989 | Palsgard et al. . | |
| 5,036,865 | 8/1991 | Keaton | 128/848 |
| 5,081,447 | 1/1992 | Echols . | |
| 5,113,176 | 5/1992 | Harris . | |

*Primary Examiner*—Robert A. Hafer
*Assistant Examiner*—Michael O'Neill
*Attorney, Agent, or Firm*—Richard C. Litman

[57] ABSTRACT

A plurally pocketed belt is wearable by a sleeping person, and provides for pressure responsive alerting devices to be inserted within one or more of the pockets. The pockets are preferably disposed in the central back, lateral, and/or rearward lateral areas of the belt when the belt is being worn, thus providing a variety of placement choices for the anti-snoring devices which may be installed therein. The devices may comprise an electromechanical vibrator, activated by a pressure switch when the device is positioned between the sleeper and an underlying surface, and/or rigid, monolithic devices having multiple projections which serve to encourage the sleeper to shift positions when disposed between the sleeper and an underlying surface. The relatively non-compliant devices provide better stimulus to encourage the sleeper to shift positions than other, softer devices developed, and provide a variety of stimuli in order that a sleeper cannot become accustomed to a single type of stimulus.

3 Claims, 1 Drawing Sheet

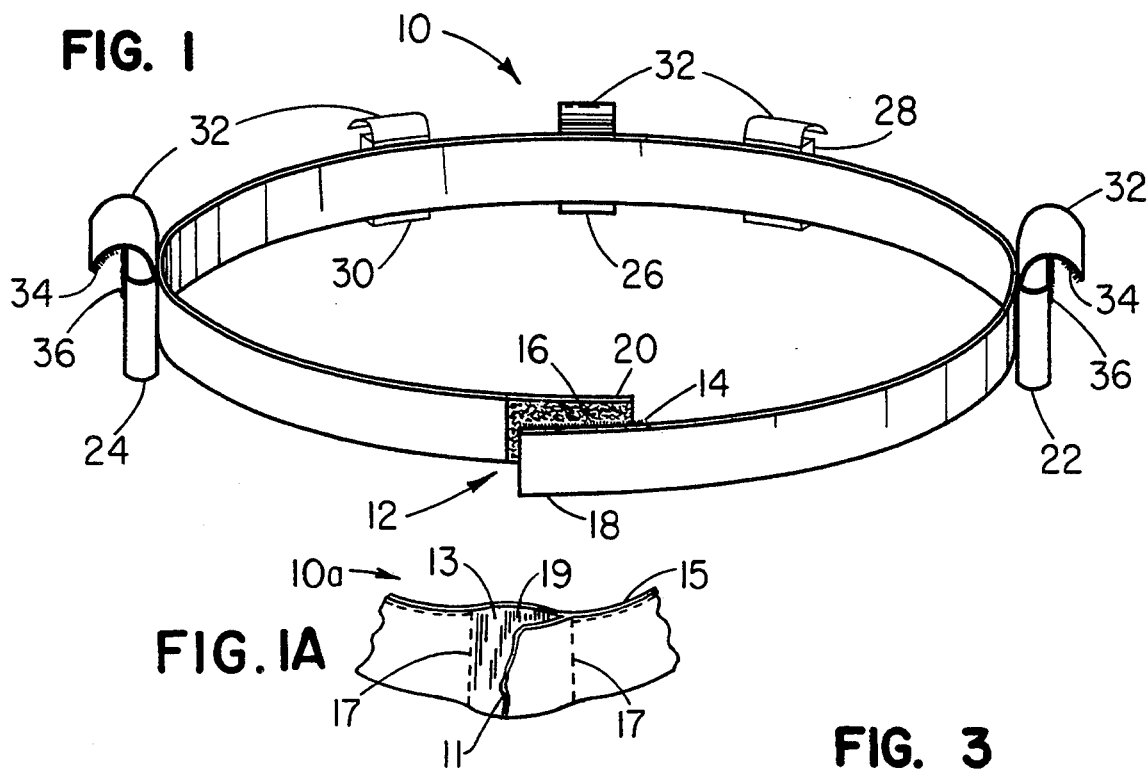
FIG. 1
FIG. 1A
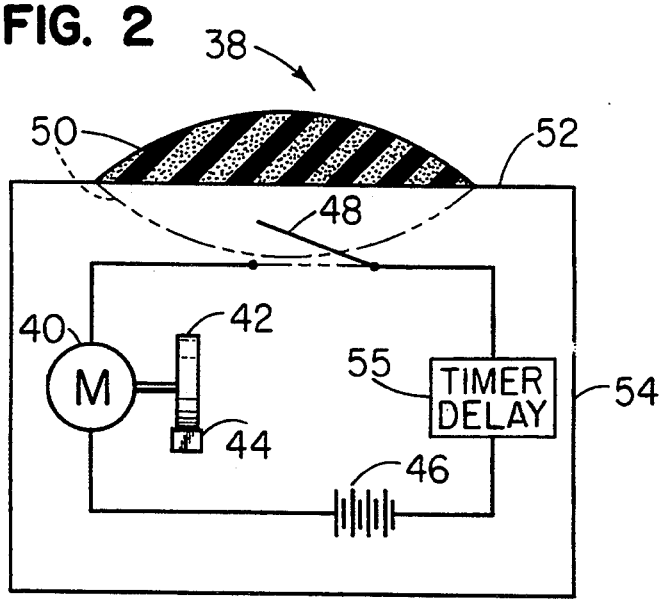
FIG. 2
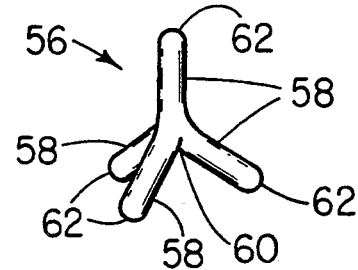
FIG. 3
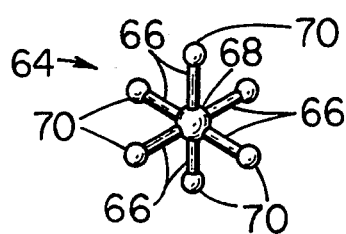
FIG. 4

ELECTROMECHANICAL TACTILE STIMULATION DEVICE WORN ON A BELT FOR THE PREVENTION OF SNORING

FIELD OF THE INVENTION

The present invention relates generally to devices for the prevention of snoring, and more specifically to a specialized belt having multiple pockets and providing for the insertion therein of devices which encourage a sleeper to assume a position less conducive to snoring.

BACKGROUND OF THE INVENTION

While snoring is often regarded as a somewhat humorous occurrence, it can be anything but humorous for those involved and for persons in te vicinity. Indeed, those who may be with a snoring person can often find it difficult or impossible to fall to sleep themselves, and in many cases the act of snoring has been known to wake the snorer, perhaps many times during the course of sleep. Further, the act of snoring tends to dry the mouth, which is at least uncomfortable for the snorer when he or she awakes, and is also associated with sleep apnea, a momentary cessation of respiration, which condition can lead to at least some degree of hypoxia on the part of the person so afflicted.

Snoring is caused by inhalation through the mouth, rather than through the nose, and the inrush of air through the throat creates a harmonic vibration or flutter of the soft palate and uvula of the snorer. Accordingly, numerous devices and means have been developed in attempts to reduce or eliminate oral breathing during sleep. Many of these devices comprise masks or articles which are applied to the area of the mouth in some way, with the intent of reducing the intake of air through the mouth, and accordingly fall beyond the scope of the present invention. Other devices have been developed which encourage the sleeper to turn to a position in which the wide opening of the jaw and mouth are less likely, in order to reduce snoring. An example of such is the well known attachment of a tennis ball to the back of a sleeper's night wear. This device has been only marginally successful, as the relatively soft and pliable tennis ball provides sufficient compliance that a sleeper can become acclimated to such after a time, and the device loses its effectiveness. Other devices which encourage a sleeper to change his or her position have been developed, as will be discussed below, but all include one or more deficiencies making them less than optimally suitable for the task.

The need arises for a belt which may be worn by a sleeping person, which belt provides a plurality of pockets for the inclusion of one or more articles at strategic locations and which articles encourage the sleeper to shift his or her position to one less likely to allow the sleeper to snore. The pocketed belt should provide plural pockets in several locations, thus allowing the insertion of one or more anti-snoring devices in locations found to be particularly effective with a given individual. The devices themselves may be electromechanical or simple, monolithic structures, and should provide sufficient effectiveness to preclude a sleeper becoming used to the devices' function. Finally, the devices should provide only for the disturbing of the sleeper, rather than producing an aural or other signal which might awaken another person sleeping in the immediate area.

DESCRIPTION OF THE PRIOR ART

U.S. Pat. No. 4,788,533 issued to Jean C. Mequignon on Nov. 29, 1988 discloses a Device For Interrupting The Snoring Of A Sleeping Person. The device is an electronic apparatus which operates by detecting sounds (not limited to snoring) above a predetermined threshold. The device then emits a sound to awaken the snoring sleeper. The device is deficient in that (1) it may trigger an alarm due to another sound source than the snorer, and (2) the audible alarm is about as likely to awaken another nearby sleeper as the snorer, particularly if the nearby person is a light sleeper.

U.S. Pat. No. 4,848,360 issued to Gote Palsgard et al. on Jul. 18, 1989 discloses a Device For Preventing Of Snoring comprising an electronic device to detect the sound of a person snoring. The device is somewhat more complex than the Mequignon apparatus discussed immediately above, including means to differentiate the sound of snoring from other sounds. The only means disclosed to awaken the snoring person are the provision of an audible signal as in the case of Mequignon above, or some means (not specifically disclosed) to cause the movement of the snorer's pillow. As in the case of the Mequignon device, it is strictly dependent upon detecting the sound of a person already snoring, by which time it is too late to prevent such. The devices serve only to prevent the continuation of snoring, rather than to eliminate any snoring at all, as in the case of the present invention. Moreover, neither Mequignon nor Palsgard et al. influence the sleeper to change position to eliminate snoring, as in the case of the present invention.

U.S. Pat. No. 5,081,447 issued to Wilford R. Echols on Jan. 14, 1992 discloses a Keep Off Your Back Alarm comprising plural gravity actuated switches on a belt or headband. The switches are disposed toward the uppermost part of the belt or band when the sleeper is resting upon his or her back, and are adapted to trigger an alarm when the sleeper is in that position. The alarm may take the form of a single vibrating device, similar to one of the means of the present invention. The present invention provides for both tactile and vibratory devices; even in the event of a single vibratory device being installed in one of the plural pockets of the present invention, tactile stimulus would be provided due to the bulk of the vibrator device. Moreover, at least the switches themselves of the Echols device are located in positions which would be uncomfortable to the sleeper when lying upon his/her side or stomach, which the gravity switches encourage the sleeper to do. Audio alarm means are also disclosed, unlike the present invention. Finally, the Echols belt must provide for electronic interconnection between the plural switches and the separate single alarm device; the present invention requires no such electronic circuitry within the belt itself.

U.S. Pat. No. 5,113,176 issued to Frank W. Harris on May 12, 1992 discloses a Lumber Roll With Audible Alerting Capability. The device includes a pressure activated switch, but also includes time delay means to activate an audible alarm if the pressure activated switch is later closed for a predetermined amount of time. Further, the device includes an automatic shutoff if no movement is detected for a given time period. With the timer delays and automatic shutoff features, the device would not provide timely stimulation to a snorer, and moreover might shut off if the snorer remained stationary for some time.

In addition to the above discussed patents, the following patents are generally related to the prevention of snoring: U.S. Pat. No. 648,028 issued to Josephus Hooper on Apr. 24, 1900 for a Device For Preventing Mouth Breathing; U.S. Pat. No. 746,869 issued to Stillman A. Moulton on Dec. 15, 1903 for a Device For Preventing Snoring; U.S. Pat. No. 1,354,652 issued to Richard H. Jeffries on Oct. 5, 1920 for a Device To Prevent Mouth Breathing; U.S. Pat. No. 2,178,128 issued to Donald H. Waite on Oct. 31, 1939 for an Antisnoring Device; U.S. Pat. No. 2,627,268 issued to Elsa L. Leppich on Feb. 3, 1953 for an Antisnoring Device; and U.S. Pat. No. 4,817,636 issued to Thomas H. Woods on Apr. 4, 1989 for an Anti-Snoring Device. The six patents listed in the immediate paragraph are all related to masks or appliances installable in or over the mouth to reduce or prevent the opening of the mouth, particularly during sleep. As such, they are not seen to relate to the structure of the present invention.

None of the above noted patents, taken either singly or in combination, are seen to disclose the specific arrangement of concepts disclosed by the present invention.

SUMMARY OF THE INVENTION

By the present invention, an improved apparatus for the prevention of snoring is disclosed.

Accordingly, one of the objects of the present invention is to provide an improved snoring preventive apparatus which comprises a plurally pocketed belt securable around a person, either directly or over night wear.

Another of the objects of the present invention is to provide an improved belt in which the plural pockets are strategically located adjacent the back, sides and/or rearward lateral areas of the person when the belt is worn.

Yet another of the objects of the present invention is to provide an improved belt which provides for the containment of device(s) which encourage the wearer to shift or adjust his or her position when the device(s) is/are disposed between the sleeper and an underlying surface.

Still another of the objects of the present invention is to provide an improved belt in combination with an electromechanical device activated by a pressure switch and providing a vibration to encourage the sleeper to change positions when the device is disposed between the sleeper and an underlying surface.

A further object of the present invention is to provide an improved belt in combination with a monolithic device having multiple projections, which projections encourage a sleeper to shift positions when the device is disposed between the sleeper and an underlying surface.

An additional object of the present invention is to provide an improved belt which provides for the secure enclosure of such snoring preventive devices.

Another object of the present invention is to provide an improved belt which includes sufficient pockets in sufficient locations to allow the placement of snoring preventive devices as desired for maximum efficiency for any given individual's needs.

A final object of the present invention is to provide an improved apparatus for the purposes described which is inexpensive, dependable and fully effective in accomplishing its intended purpose.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

FIG. 1 is a perspective veiw of the belt of the present invention, showing the plurality of pockets and their various locations on the belt, as well as the closure means and other details.

FIG. 1A is a broken away perspective view of an alternate belt and pocket construction means.

FIG. 2 is a pictorial schematic of an electromechanical vibrating device usable with the belt of the present invention.

FIG. 3 is a perspective view of a device having four projections and usable with the belt of the present invention.

FIG. 4 is a perspective view of a device having six mutually orthogonal projections and usable with the belt of the present invention.

Similar reference characters denote corresponding features consistently throughout the several figures of the attached drawings.

DETAILED DESCRIPTION OF THE PREFERRED EMBODIMENTS

Referring now to the drawings, the present invention will be seen to relate to a belt 10 providing for the containment of articles for the prevention of snoring. Belt 10 includes a front closure means 12, such as the mating first and second hook and loop fastening material portions 14 and 16 at the respective first and second ends 18 and 20 of the belt 10. Alternative closure means may be used as desired (e.g., snaps, buckle, buttons, etc). However, the mating hook and loop material portions 14 and 16 provide a relatively smooth front closure means to provide good comfort to a prone sleeper wearing such a belt 10.

Belt 10 further includes one or more pockets installed along the outside surface of the belt 10, which pockets provide for the containment of devices for the prevention of snoring and are discussed in detail further below. FIG. 1 shows left and right lateral pockets 22 and 24; a medial dorsal pocket 26; and left and right dorsal pockets 28 and 30, installed upon corresponding portions of the belt 10. (Left and right directions will be seen to be reversed in FIG. 1 due to the facing arrangement of the belt 10 in the drawing.) It should be understood that the belt 10 of the present invention may not necessarily include all of the pockets shown, but preferably at least two of the above located pockets will be provided on a single belt 10.

Each of the pockets 22 through 30 includes a closure flap 32 closable by mating hook and loop fastening material portions 34 and 36, as in the case of the first and second belt ends 18 and 20, or alternatively by other means. Thus, each of the pockets 22 through 30 is securely closable to contain an article therein completely and prevent its escape due to movement of the wearer of the belt during sleep.

FIG. 1A discloses an alternative construction of a belt 10a, formed of a doubled over sheet of material to form outer and inner layers 11 and 13. The belt 10a is sewn or otherwise secured along one edge 15, with intermittent spaced apart vertical separations 17 provided along the belt 10a. The edge 15 is left open between these vertical separations to form a series of pockets 19 integral with the belt 10a. It will be understood that only a single pocket 19 is described, but such a pocket 19 may be formed in the dorsal, lateral, and/or medial dorsal areas of the belt 10a, in the manner of the installation of pockets 22 through 30 of belt 10. In any case, both belts 10 and 10a are preferably formed of a relatively soft, pliable and flaccid material, in order to preclude sleep disturbance due to the belt and/or pockets themselves when empty. Only the tactile devices themselves should disturb the sleep of the wearer of the belt 10/10a when installed in the pockets 19 or 22 through 30.

FIG. 2 discloses an electromechanical vibrator device 38 insertable in one (or more, in the case of plural devices 38) of the pockets 22 through 30 of the belt 10, or pockets 19 of belt 10a. Vibrator 38 operates by means of a small electric motor 40, which drives a flywheel 42 having an eccentric weight 44 thereon. A battery or batteries 46 provide power for the motor 40. A normally open switch 48 is provided in series with the motor 40 and battery/batteries 46, for the operation of the vibrator 38. The switch 48 is closed by means of a pliable switch cover 50 in the outer or inner facing side 52 of the vibrator case 54. The case 54 is preferably relatively hard and rigid, in order to (1) protect the contents, and (2) to provide some inherent tactile stimulation when interposed between a sleeper and underlying surface. Thus, when the switch cover 50 is compressed, as by the weight of a person resting on the vibrator 38, the cover 50 defects inward to push the normally open switch 48 to a closed position and activate the motor 40. The resulting rapid rotation of the unbalanced flywheel 42 results in a vibration of the vibrator device 38, which vibration is annoying to the sleeper and serves to cause the sleeper to change position. As weight or pressure is removed from the switch cover 50, pressure is relaxed on the normally open switch 48, which springs back to open the circuit and cause the motor 40 to cease operation. The vibrator 38 is relatively quiet in operation, thus allowing other sleepers in the immediate vicinity to continue their sleep and affecting only the sleeper wearing such a device(s) 38 in one of the pockets 22 through 30 of the belt 10. Other means of creating the required vibration may be adapted, if desired, e.g., make-and-break points, etc. In order to preclude the activation of the vibrator 38 due to transient movements during sleep, a timer delay device 55 may be placed in series with the motor 40 and switch 48. The delay may be set as desired, from one to several seconds, in order to allow the sleeper to transition from one position to another without setting off the alarm. Under certain circumstances, provision may be made for a longer delay of up to several minutes, e.g., when a person is resting upon his/her back prior to going to sleep. In any case, it will be seen that the device 38 is capable of providing both vibratory stimulus, as discussed above, and also tactile stimulation due to the bulk and relatively hard structure of the case 54, thus precluding a sleeper from becoming used to a single type of stimulus from the device 38.

FIGS. 3 and 4 provide perspective views of other types of tactile stimulative devices which may be placed in one or more of the pockets 22 through 30 of the belt 10. The tactile device 56 of FIG. 3 includes at least four projections 58 radiating in three dimensions from a common center point 60. The precise number of projections is unimportant, so long as there are a sufficient number to insure that at least one will always be disposed out of a plane defined by any other projections. It will be further noted that each of the projections 58 has a relatively blunt tip 62, in order to preclude injury to a sleeper using such a device 56. FIG. 4 shows an alternative tactile stimulative device 64, having six projections 66 radiating from a common center point 68 along three mutually orthogonal axes. As in the case of the tactile device 56 discussed above, each of the projection 66 has a relatively blunt tip 70, to preclude injury to the user. Both tactile devices 56 and 64 are preferably formed as a single, rigid monolithic unit, in order to prevent their collapse due to pressure or weight being placed upon them. Yet, the relatively blunt tips 62 or 70 preclude any hazard.

Snoring most often occurs when a sleepr is lying on his/her back, and the sleeper's jaw and mouth are allowed to open. It has been found that persons who sleep on their sides, and particularly on their stomachs in a prone position, are less likely to snore; sleeping in a prone position greatly reduces the likelihood of snoring. Accordingly, a potential snorer may don the belt 10 (or 10a) of the present invention with the closure means to the front and the pockets 22 through 30 (or 19) disposed to the sides and back of the belt 10/10a and its wearer. Assuming that the person has found that no snoring occurs when he/she sleeps on one side or prone, then it may only be necessary to install a tactile stimulation device (such as the vibrator 38 of FIG. 2, or one of the tactile devices 56 or 64 of FIGS. 3 and 4) in a single central dorsal pocket 26/19 of the belt 10/10a. On the other hand, if the person has been found to snore while sleeping upon his/her side, it may be necessary to place additional tactile devices 38, 56 and/or 64 in the left and right dorsal pockets 28 and 30, and/or in the left and right lateral pockets 22 and 24 of belt 10, or in pocket(s) 19 in like locations of a belt 10a. In any case, tactile stimulation resulting from the person turning to place any of the devices 38, 56 and/or 64 between him/her and an underlying surface, will result in some tactile stimulation and discomfort to the person. In the case of the electromechanical vibrator 38 of FIG. 2, the pressure switch 48 will be activated when the pliable switch cover 50 is compressed due to weight or pressure and the timer delay switch 55 closes after some predetermined delay period, and the vibration of the eccentric weighted wheel 42 will create some discomfort to the sleeper and cause him/her to change his/her position to remove the pressure from the vibrator 38 to open the switch 48. As noted above, the bulk and rigidity of the case 54 may also serve to disturb the sleeper, in combination with the vibratory sensations provided when the device 38 is activated, thus simultaneously providing two different sensations to disturb the sleeper and induce him/her to change position.

The use of such a vibrator 38 may be sufficient to cause many sleepers to change their position to one not allowing snoring to occur, while some sleepers may require more harsh stimulation. The tactile stimulation devices 56 and 64 are capable of providing just such stimulation when placed in an appropriate pocket(s) of the belt 10 or 10a. It will be seen that as a sleeper turns to place such a device 56 or 64 between him/her and an underlying mattress or surface, the three dimensional projections 58 or 66 will insure that at least one projection 58 or 66 will always be oriented toward the inner surface of the pocket and belt 10 or 10a, and toward the sleeper, thus irritating the sleeper and causing him/her to change positions to remove the irritation. The belt 10 of the present invention, with its included pockets 22, 24, 26, 28, and/or 30 (or belt 10a with pockets 19), will serve to provide some irritation to a sleeper who may be resting upon one or more of the pockets 22 through 30, merely due to their bulk. However, it will be seen that the front of the belt 10/10a provides a relatively smooth surface due to the flat closure means 12 preferably provided, thus encouraging a wearer of the belt 10/10a to move to a position to reduce the likelihood of snoring. As noted above, if desired at least some of the pockets, e.g., the lateral pockets 22 and 24, may be eliminated from the belt 10 if it has been found that the person can sleep upon his/her side without snoring. The relatively flat and thin belt 10/10a will cause no discomfort in such a situation, and serves to allow the wearer to sleep peacefully unless the sleeper turns to place a pocket containing one of the devices 38, 56 or 64 between him/her and the underlying surface and thus cause irritation to encourage the sleeper to change his/her position to a more comfortable one. Further, it may be that some snorers may respond better to a variety of stimuli, such as the vibration produced from the device 38 and/or the intrusion of the projections of the devices 56 and 64 of FIGS. 3 and 4. Accordingly, these various types of devices may be installed in the pockets of belt 10/10a as desired, to provide either vibratory or intrusive stimulation to a snorer, depending upon the snorer's position and the specific pocket in which any one of the devices 38, 56 or 64 is located. Thus, a snorer will not become used to a single type of physical sensation and therefore will not tend to sleep through such a disturbance, as may occur with only a single type of tactile stimulation device.

It is to be understood that the present invention is not limited to the sole embodiments described above, but encompasses any and all embodiments within the scope of the following claims.

We claim:

1. An apparatus for the prevention of snoring by a user of said apparatus, comprising:

a belt having first and second ends with cooperating frontal closure means thereon, a left dorsal portion, a right dorsal portion, a medial dorsal portion, a left lateral portion and a right lateral portion, and plural pockets installed along said belt, wherein said left dorsal portion, said right dorsal portion, said medial dorsal portion, said left lateral portion and said right lateral portion each includes at least one of said pockets, whereby said belt is worn about a torso of a user;

at least one tactile stimulation device, wherein said at least one tactile stimulation device is installed in at least one of said dorsal pockets, and in at least one of said lateral pockets;

said tactile stimulation device includes a battery powered electromechanical device having a motor driving an eccentrically balanced wheel and activated by a pressure sensitive switch when said pressure sensitive switch is located between the underlying surface and the torso of the user, whereby said eccentrically balanced wheel produces a vibration when said motor is activated by means of said pressure sensitive switch;

whereby when said tactile stimulation device is between the user and an underlying surface, said tactile stimulation device provides tactile stimulation to the user, whereby the user changes sleeping positions in response to the tactile stimulation.

2. The apparatus of claim 1 including:

timer delay means installed in series with said electromechanical device and said pressure sensitive switch.

3. The apparatus of claim 1 including:

a rigid and hard case surrounding said electromechanical device, whereby said case provides tactile discomfort in combination with vibration when said electromechanical device is interposed between a person and an underlying surface and said motor is activated.

* * * * *